(12) United States Patent
Arends et al.

(10) Patent No.: US 9,297,750 B2
(45) Date of Patent: Mar. 29, 2016

(54) METHODS AND APPARATUS FOR AN OPTICAL SYSTEM OUTPUTTING DIRECT LIGHT AND HAVING A SENSOR

(71) Applicant: FiftyThree, Inc., New York, NY (US)

(72) Inventors: Thomas C. Arends, Bellevue, WA (US); Nicholas E. Bratt, Edmonds, WA (US); John K. Ikeda, Seattle, WA (US); Jonathan R. Harris, Redmond, WA (US); Georg F. Petschnigg, New York, NY (US)

(73) Assignee: FiftyThree, Inc., New York, NY (US)

( * ) Notice: Subject to any disclaimer, the term of this patent is extended or adjusted under 35 U.S.C. 154(b) by 304 days.

(21) Appl. No.: 13/828,928

(22) Filed: Mar. 14, 2013

(65) Prior Publication Data
US 2014/0268161 A1    Sep. 18, 2014

(51) Int. Cl.
*G01N 21/47*    (2006.01)

(52) U.S. Cl.
CPC .................................. *G01N 21/4738* (2013.01)

(58) Field of Classification Search
CPC .................................................. G01N 21/4738
See application file for complete search history.

(56) References Cited

U.S. PATENT DOCUMENTS

| 7,670,070 | B2 | 3/2010 | Craven-Bartle |
| 7,868,878 | B2 | 1/2011 | Craven-Bartle et al. |
| 2005/0073508 | A1 | 4/2005 | Pittel et al. |
| 2007/0013661 | A1* | 1/2007 | Theytaz et al. ............... 345/166 |
| 2010/0021022 | A1 | 1/2010 | Pittel et al. |
| 2011/0007037 | A1 | 1/2011 | Ogawa |
| 2011/0090178 | A1 | 4/2011 | Lai et al. |
| 2011/0310066 | A1 | 12/2011 | Fermgard et al. |
| 2014/0267185 | A1 | 9/2014 | Arends et al. |

OTHER PUBLICATIONS

Office Action for U.S. Appl. No. 13/823,907, mailed Apr. 2, 2015.

* cited by examiner

*Primary Examiner* — Sahlu Okebato
(74) *Attorney, Agent, or Firm* — Cooley LLP (57) ABSTRACT

In some embodiments, an apparatus includes a housing and an image sensor that is coupled to the housing. The apparatus also includes a non-imaging optical system coupled to the housing that can output light to a surface and produce a scattered light component and a specular reflected light component. The image sensor and the non-imaging optical system are collectively configured in such a manner that during operation, the image sensor receives from a surface (1) at least a portion of the scattered light component and not the specular reflected light component or (2) at least a portion of the scattered light component having a magnitude and at least a portion of the specular reflective light component having a magnitude less than the magnitude of the portion of the scattered light component.

17 Claims, 5 Drawing Sheets

METHODS AND APPARATUS FOR AN OPTICAL SYSTEM OUTPUTTING DIRECT LIGHT AND HAVING A SENSOR

CROSS-REFERENCE TO RELATED APPLICATIONS

This application is related to co-pending U.S. nonprovisional patent application Ser. No. 13/282,907, entitled "Methods and Apparatus for an Optical System Outputting Diffuse Light and Having a Sensor,"filed Mar. 14, 2013, the same filing date as this application, and which is incorporated by reference herein in its entirety.

BACKGROUND

The embodiments described herein relate generally to methods and apparatus for a dark field illumination system. More specifically, the embodiments described herein relate to methods and apparatus for an optical system outputting direct light and having a sensor.

Pen strokes by handheld devices such as electronic pens or styluses on display surfaces can be digitally recorded by optical tracking systems contained within the handheld devices. The optical tracking systems typically include miniaturized cameras or sensors that can digitally recorded the pen strokes on the display surfaces. Known optical tracking systems use opaque dots to register position with a digital pen. These dots are typically invisible to the naked eye but detectable by the optical tracking system. Such known optical tracking systems typically use a wide field of view to receive sufficient reflections from the dots and have relatively low resolution.

Accordingly, a need exists for an improved methods and apparatus for the accurate and high resolution determination of position information of handheld devices on display surfaces.

SUMMARY

In some embodiments, an apparatus includes a housing and an image sensor that is coupled to the housing. The apparatus also includes a non-imaging optical system coupled to the housing that can output light to a surface and produce a scattered light component and a specular reflected light component. The image sensor and the non-imaging optical system are collectively configured in such a manner that during operation, the image sensor receives from a surface (1) at least a portion of the scattered light component and not the specular reflected light component or (2) at least a portion of the scattered light component having a magnitude and at least a portion of the specular reflective light component having a magnitude less than the magnitude of the portion of the scattered light component.

DETAILED DESCRIPTION

In some embodiments, an apparatus includes a housing and an image sensor that is coupled to the housing. The apparatus also includes a non-imaging optical system coupled to the housing that can output light to a surface and produce a scattered light component and a specular reflected light component. The image sensor and the non-imaging optical system are collectively configured in such a manner that during operation, the image sensor receives from a surface (1) at least a portion of the scattered light component and not the specular reflected light component or (2) at least a portion of the scattered light component having a magnitude and at least a portion of the specular reflective light component having a magnitude less than the magnitude of the portion of the scattered light component.

In some embodiments, an apparatus includes a housing and an image sensor coupled to the housing that has a field of view. The apparatus also includes a non-imaging optical system coupled to the housing that can output light from at least a first location of the housing and a second location of the housing with at least a portion of the field of view being between the first location and the second location and excluding the first location and the second location. The image sensor can receive from a surface at least one of (1) a scattered light component associated with the first location, or (2) a scattered light component associated with the second location.

In some embodiments, an apparatus includes a stylus housing that can be used with an electronic device. The apparatus includes an image sensor coupled to the stylus housing and the image sensor defines an optical axis and has a field of view. The apparatus also includes a non-imaging optical system coupled to the stylus housing that can output light to a surface along an optical path having an optical axis non-parallel to the optical axis of the image sensor to produce a specular reflection. The non-imaging optical system and the image sensor can be collectively configured such that the image sensor does not receive the specular reflection.

As used in this specification, the singular forms "a," "an" and "the" include plural referents unless the context clearly dictates otherwise. Thus, for example, the term "an image sensor" is intended to mean a single image sensor or multiple image sensors.

As used in this specification, the terms "housing" and "stylus housing" relate to, or example, the outer container or cover of an imaging apparatus that holds all the optical, electronic and mechanical components of the imaging apparatus, and can be used interchangeably unless the context clearly dictates otherwise.

Figure 1:
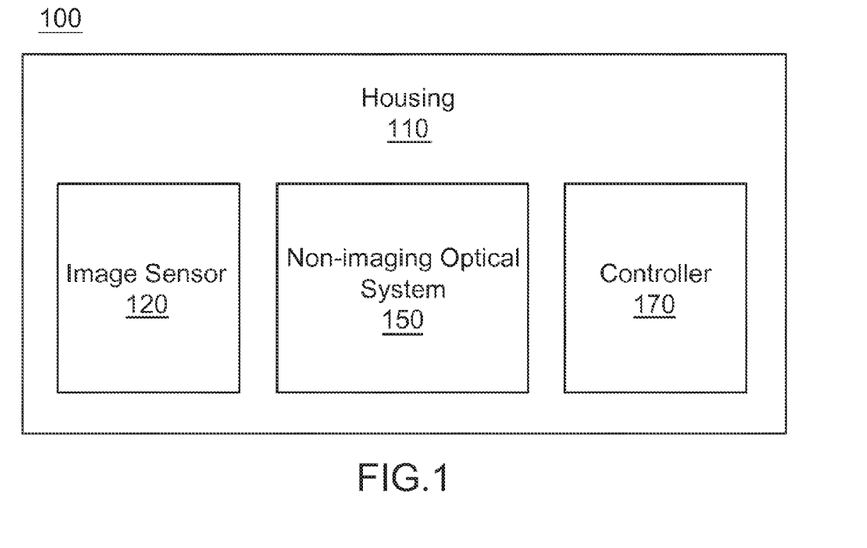
FIG. 1 is a block diagram of an imaging apparatus, according to an embodiment.

FIG. 1 is a block diagram of an imaging apparatus, according to an embodiment. The imaging apparatus 100 includes a housing 110, an image sensor 120 coupled to the housing 110 and having a field of view, a non-imaging optical system 150 coupled to the housing 110, and a controller 170 coupled to the housing 110. The housing 110 can be made of, for example, plastic, steel, aluminum, etc. The housing 110 can be elongate and pen-shaped, and can include one or more parts that can carry or enclose other parts of the imaging apparatus 100 such as, for example, the image sensor 130, the non-imaging optical system 150, the controller 170, and a battery (not shown in FIG. 1). Each of the compartments of the housing 110 can be, for example, accessible via a fully or semi-detachable lid. The housing 110 can also define one or more spaces for one or more printed circuit boards (PCB) that can contain the electronics for determining the accurate position information associated with the imaging apparatus 100. The housing 110 can define, for example, a first opening through which the illumination can be sent from the non-imaging optical system 150, a second opening through which images can be captured by the image sensor 120 and a third opening through which a stylus of the writing tip (not shown) can protrude or extend.

The image sensor 120 is coupled to and/or disposed within the housing 110 of the imaging apparatus 100, and has a field of view (FOV) and an optical axis. The image sensor 120 can detect the power of the scattered light and the power of the specular reflected light. The image sensor 120 can be arranged to define an object plane and an image plane, where an object that is located in a field of view in the object plane is reproduced as an image in the image plane. The image sensor 120 can also include a photo-detector that is substantially co-located with the image plane to physically or electronically capture the image. Such a photo-detector can be, for example, a photomultiplier tube (PMT), a charge coupled device (CCD) camera, a photodiode array detector, a pixel array detector, an avalanche photodiode (APD), and/or the like.

In some configurations, the image sensor 120 and the non-imaging optical system 150 can be collectively set up or configured such that the image sensor 120 can receive at least a portion of the light scattered and reflected from a surface (e.g., a film) after being illuminated by the non-imaging optical system 150. In some configurations, the image sensor 120 and the non-imaging optical system 150 can be collectively configured such that, during operation of the imaging apparatus 100, the image sensor 120 receives from a surface (1) at least a portion of the scattered light component and not the specular reflected light component or (2) at least a portion of the scattered light component having a magnitude and at least a portion of the specular reflective light component having a magnitude less than the magnitude of the received scattered light component.

After detecting the power of the scattered and/or specular reflected light, the image sensor 120 can send an output voltage to, for example, a control module (not shown in FIG. 1). In some configurations, the control module can be part of the controller 170. In other configurations, the control module can be, for example, a hardware module and/or software module stored in a memory and/or executed in a processor on a printed circuit boards (PCB) of the imaging apparatus 100. In some configurations, the image sensor 120 can include optional beam shaping/collection lenses that can enhance the efficiency of scattered light collection. In yet other configurations, the image sensor 120 can include two or more photo-detectors to establish multiple imaging pathways.

The non-imaging optical system 150 can include light sources such as, for example, light emitting diodes (LEDs), organic light emitting diodes (OLEDs), semiconductor laser diodes, and/or the like. Additionally, the non-imaging optical system 150 can also include optical lenses and/or prisms to efficiently deliver the illumination light to the target surface, and include electronic and/or mechanical optical shutters to select the optimal image path. In some configurations, the non-imaging optical system 150 can output illumination light to produce a specular reflected light component at a non-zero angle relative to the optical axis of the image sensor 120, where the specular reflected light component has a lobe width less than the angle.

In some configurations, the imaging apparatus 100 can include an image sensor 120 and a non-imaging optical system 150 that can include a first light source, a first optical component, a second light source and a second optical component. The first light source and the first optical component can collectively be configured to send a portion of the illumination light along a first optical path from at least a first location of the housing 110. The second light source and the second optical component can collectively be configured to send a portion of the illumination light along a second optical path from at least a second location of the housing 110, where at least a portion of the field of view of the image sensor 120 is between the first location and the second location.

The controller 170 can include, for example, one or multiple optical shutters, and/or prisms, and/or optical iris that can be used to activate one or multiple illumination pathways and/or imaging pathways. An illumination pathway is the path taken by the illumination light as it travels from a light source via one or multiple optical, electrical and/or mechanical components to impinge upon the target (e.g., a surface of a film). In some instances, an illumination pathway can also be referred to as an optical pathway or an optical path. An imaging pathway is the path taken by the scattered light and/or specular reflected light as it travels from the scattering microparticles (located within a film) and/or the surface of the target (e.g., a surface of a film) via one or multiple optical, electrical and/or mechanical components to the imaging sensor 120. The controller 170 can also be used to select one or multiple imaging pathways that can generate optimal or desired images at the image sensor 120 that has the highest signal-noise-ratio. The controller 170 can, for example, be used to calibrate the imaging apparatus 100 during a calibration mode. Additionally, the controller 170 can also be used during an application mode to accurately determine the location of the imaging apparatus 100 on a display surface.

In some configurations, the output of the controller 170 can be sent to, for example, a control module (not shown in FIG. 1) that is associated with real time image processing (or near-real-time image processing due to processing delays) that can select the optimal or desired illumination pathway and/or imaging pathway that can generate images with the highest signal-noise ratio. Hence, the controller 170 can be used to determine the location of the imaging apparatus 100 on the display surface with high resolution. In such configurations, the control module can be a hardware module and/or software module (stored in the memory and/or executed in a processor) on the printed circuit boards (PCB) of the imaging apparatus 100. Further details of the different embodiments of the imaging apparatus are described herein.

Figure 2:
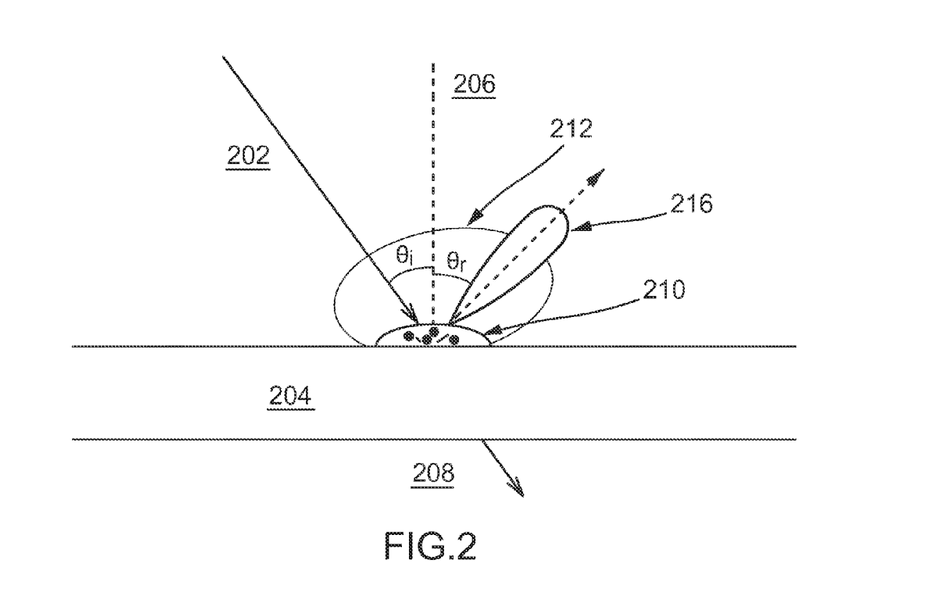
FIG. 2 is a diagram showing an example of light scattered and reflected after impinging upon a clear polyethylene terephthalate (PET) film coated with scattering microparticles, according to an embodiment.

FIG. 2 is a diagram showing an example of light scattered and reflected after impinging upon a clear polyethylene terephthalate (PET) film coated with scattering microparticles, according to an embodiment. The incident illumination 202 impinges upon the surface of the clear PET film 204 at an angle of incidence ($\theta_i$) with respect to the surface normal 206. The scattering microparticles 210 are translucent and hence a significant amount of the incident illumination passes through the clear PET film 204. Hence, approximately 50-75% of the incident illumination is transmitted through the clear PET film as the transmitted light 208 as shown in FIG. 2. The scattering of the incident illumination light 202 by the scattering microparticles 210 present on the surface of the clear PET film 204 can be dependent on a number of parameters such as, for example, the loading density of the scattering microparticles 210, the size of the scattering microparticles 210, the shape of the scattering microparticles 210, the material used in the scattering microparticle 210 fabrication, the propensity of the scattering microparticles 210 to form aggregates and other higher order structures, etc. Hence, the distribution of the scattered light 212 in some cases can be isotropic in nature.

Many applications based on optical detection assume perfect diffuse reflections and assume specular reflections to be an outlier phenomenon. In reality, however, the presence of specular reflections is inevitable. Hence, incorporating the knowledge of specular reflections is desirable to make the optical detection methods robust. For a perfectly flat and smooth surface (i.e., a perfect mirror), the direction of specular reflection 216 follows the law of reflection, which states the angle of incoming illumination $\theta_i$ and the angle of outgoing reflected light are the same ($\theta_i=\theta_r$). In many surfaces that are not perfect mirrors, however, a certain degree of specularity can also be observed in the reflected light even though the direction of reflection $\theta_r$ is not identical to the direction of incidence $\theta_i$. In other words, specular reflections do not only form a sharp line (spike) distribution of reflection, but can also form a lobe distribution. Therefore, specular reflections can form two components: (1) specular spike and (2) specular lobe 216, which is illustrated in FIG. 2. The size and shape of the lobe of the specular reflected light 216 can depend on the size and the granularity of surface imperfections. Additionally, the specular reflection lobe 216 width is also dependent on the nature of the surface roughness and scale of the surface roughness compared to the incident illumination light wavelength.

Figure 3:
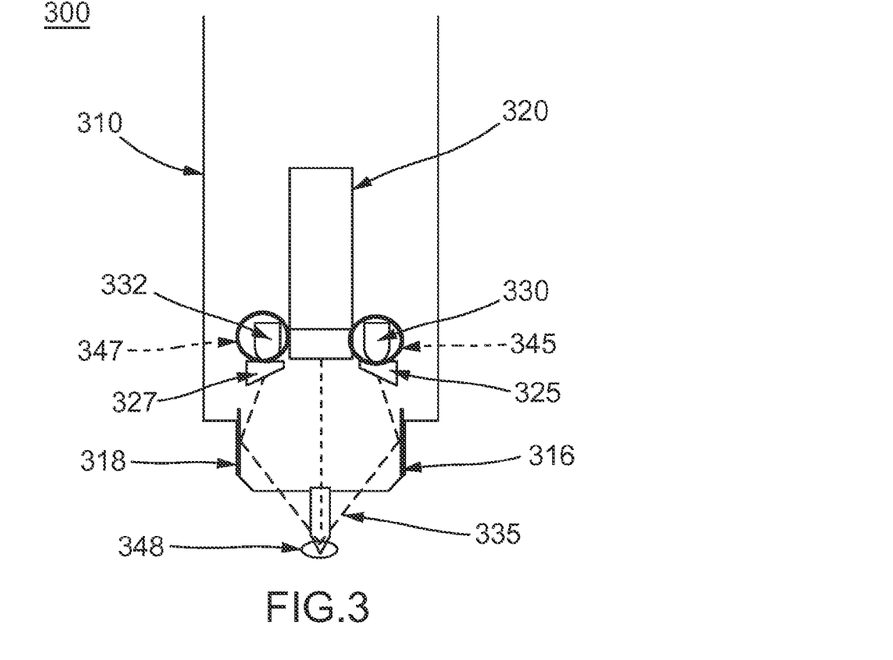
FIG. 3 is a two-dimensional (2-D) cross-section diagram of an imaging apparatus, according to an embodiment.

FIG. 3 is a two-dimensional (2-D) cross-section diagram of an imaging apparatus, according to an embodiment. The imaging apparatus 300 includes a housing 310 that combines two independent illumination light paths with a non-imaging optical system that includes a first light source (e.g., LED 330), a first refractive optical component (e.g., prism 325), a first reflective optical component (e.g., mirror 316) to reflect the incident illumination, a second light source (e.g., LED 332), a second refractive optical component (e.g., prism 327), and a second reflective optical component (e.g., mirror 318) to reflect the incident illumination.

The imaging apparatus 300 can also include an image sensor 320 that has a specifically defined field of view, a stylus 335, and any (optional) beam shaping/collection lenses (not shown in FIG. 3). The first light source (e.g., LED 330), the first refractive optical component (e.g., prisms/optics 325), and the first reflective optical component (e.g., mirror 316) can be collectively configured to send a portion of the illumination light along a first optical path from a first location of the housing 310 (e.g., location of housing 345 in FIG. 3) to, for example, the surface of a film (e.g., illumination region 348 in FIG. 3). The second light source (e.g., LED 332), the second refractive optical component (e.g., prisms/optics 327), and the second reflective optical component (e.g., mirror 318) can be collectively configured to send a portion of the illumination light along a second optical path from a second location of the housing 310 (e.g., location of housing 347 in FIG. 3) to, for example, the surface of a film (e.g., illumination region 348 in FIG. 3), with at least a portion of the field of view (of the image sensor 320) being between the first location 345 and the second location 347. The non-imaging optical system of the imaging apparatus 300 is coupled to the housing 310 and can output light from at least a first location of the housing (e.g., location of housing 345 in FIG. 3) and a second location of the housing (e.g., location of housing 347 in FIG. 3), where at least a portion of the field of view (of the image sensor 320) is between and excludes the first location and the second location. The image sensor 320 can receive from a surface of the film (e.g., the illumination region 348) at least one of a scattered light component associated with the first location (contained within the illumination region 348) and/or a scattered light component associated with the second location (contained within the illumination region 348).

The image sensor 320 and the non-imaging optical system can be collectively configured such that the image sensor 320 either: (1) does not receive a specular reflected light component associated with or generated from the illumination light; or (2) receives a specular reflected light component associated with the illumination light that has a magnitude less than a magnitude of the at least one of the scattered light component associated with the first location (contained within the illumination region 348) or the scattered light component associated with the second location (contained within the illumination region 348). FIG. 3 shows the imaging apparatus 300 to have two independent illumination light paths as a way of example only, and not by limitation. In other configurations, the imaging apparatus 300 can include more than two illumination light paths that can either be distributed radially symmetrically or radially non-symmetrically about the optical axis of the image sensor 320.

The imaging apparatus 300 has a specified angle(s) between the chief ray of each of the two LED's 330 and 332 and the center of the imaging field. The imaging apparatus 300 can also have a specified optimum distance between the illumination sources (e.g., LEDs 330 and 332) and the target surface that can allow image formation with highest or desired signal-noise-ratio and the highest or desired rejection of specular reflection. The two non-imaging (or illumination) paths defined by the LEDs 330 and 332 and the prism/optics 325 and 327 may or may not be symmetrically deployed about the center of the imaging field. In some configurations, more than two independent light paths can be used. Additionally, the two light paths shown in FIG. 3 can be activated independently or in defined combinations with respect to one another. The non-imaging optical system in the imaging apparatus 300 includes prisms (or Fresnel prisms) 325 and 327 that can be used to advantageously redirect the LED light to strike the target surface. In some configurations, the non-imaging optical system can also include surfaces that have focusing and/or beaming properties. In other configurations, the non-imaging optical system can, optionally, include additional mirrors to advantageously redirect the LED light to strike the target surface and/or increase the collection efficiency of the scattered light.

Under certain orientations of the imaging apparatus 300, specular reflected light can reflect back into the image sensor 320 of the imaging apparatus 300. Because the specular reflected light is of greater intensity than the scattered light (from the scattering microparticles), the specular reflected light can dominate the image if the specular reflected light is in the field of view of the image sensor 320. This can significantly reduce the contrast (and signal-noise-ratio) of the images formed on the image sensor 320. The amount of specular reflected light reflecting back into the image sensor 320 can depend on several parameters such as, for example, the field of view of the image sensor 320, the tilt of the housing 310 with respect to the surface (of the film), the orientation of the light source with respect to the optical axis of the image sensor 320, the presence of collimating and/or focusing lenses in both the illumination pathway and the imaging pathway, and/or the like. The specular reflected light can be prevented from reaching (or being detected by) the image sensor 320 if the angle of incidence and reflection (that includes the entire specular lobe) can be made to lie outside the field of view of the image sensor 320. Hence, the prism/optics 325 and/or 327 and any additional optical components that form or are part of a controller for the imaging apparatus 300 that can selectively activate the first light source (e.g., LED 330) or the second light source (e.g., 332) based on an orientation of the housing 310 relative to the surface of the film. Additionally, depending on the particular construction, the imaging apparatus 300 can avoid specular reflections caused by tilt angles that naturally result from either left-handed or right-handed users.

The LEDs 330 and 332 of the imaging apparatus 300 are shown in FIG. 3 by way of example only, and not by limitation. In other configurations, the light sources in the imaging apparatus 300 can be, for example, semiconductor laser diodes (instead of LEDs). In such configurations, each laser light source can generate a substantially collimated incident illumination beam. The substantially collimated incident beam can be made to travel though one or multiple focusing lenses to produce an illumination region (e.g., illumination region 348 in FIG. 3) on the surface of the target (e.g., a film or foil on a display surface). A robust optical alignment of the two illumination lightpaths can lead to a relatively strong incident power being delivered to the target surface (that can significantly increase the magnitude of the scattered light). In some embodiments, the conventional optical components as shown in FIG. 3 can be replaced with Fresnel prisms and other diffractive optical elements. This can help in miniaturization of the imaging apparatus 300.

Figure 4:
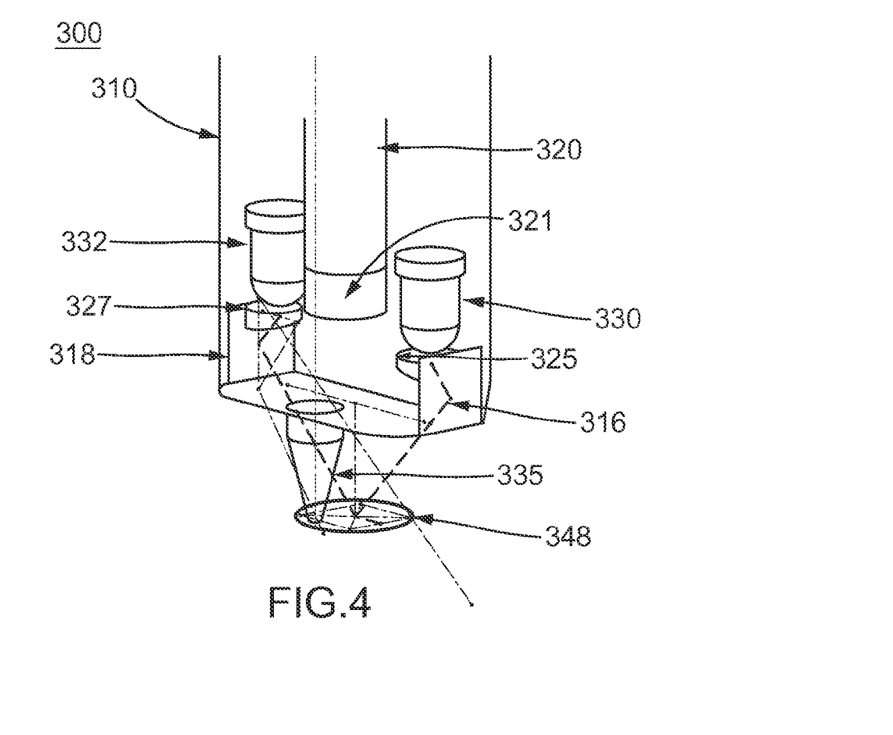
FIG. 4 is a three-dimensional (3-D) illustration of the cross-sectional image of the imaging apparatus in FIG. 3.

FIG. 4 is a three-dimensional (3-D) illustration of the cross-sectional image of the imaging apparatus of FIG. 3. In FIG. 4, the housing 310 of the imaging apparatus 300 is illustrated in a semi-transparent mode for viewing the different optical components contained within the housing 310. The imaging apparatus 300 includes the image sensor 320, a housing for the imaging lens 323, light sources such as the LEDs 330 and 332, refractive optical components such as the prisms 325 and 327, reflective optical components such as the mirrors 316 and 318, and the stylus 335 that is at least partly contained within the housing 310 and partly protrudes outside the housing 310. FIG. 4 shows that the illumination region 348 (i.e., the region where the incident illumination beam strikes the surface of the film) is located a certain pre-determined distance away from the stylus 335. As mentioned above, the incident illumination can generate both specular reflected light from the surface of the film and scattered light from the scattering microparticles contained within the film. Hence, at least a portion of the field of view of the image sensor 320 overlaps with the illumination region 348 so that the scattered light can be detected by the imager sensor 320. Additionally, the image sensor 320 and the non-imaging optical system can be collectively configured such that the image sensor 320 either: (1) does not receive a specular reflected light component associated with the illumination light or; (2) receives a specular reflected light component associated with the illumination light that has a magnitude less than a magnitude of the received scattered light component within the image sensor 320 field of view. The spatial distance between the stylus 335 and the illumination region 348 can be determined or calibrated, for example, in terms of number of pixels in the x and y lateral directions to allow the imaging apparatus to accurately determine the location of the stylus 335 with respect to the surface of the film.

Figure 5:
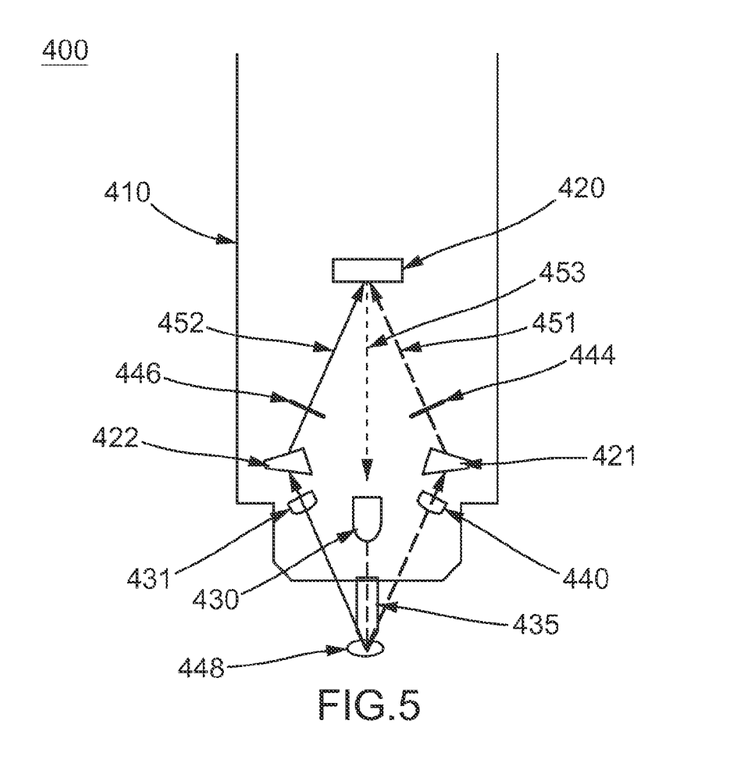
FIG. 5 is a two-dimensional (2-D) cross-section diagram of an imaging apparatus, according to another embodiment.

FIG. 5 is a two-dimensional (2-D) cross-section diagram of an imaging apparatus, according to another embodiment. The imaging apparatus 400 includes a housing 410, an image sensor 420, optical shutters 444 and 446, refractive optical components such as the prisms (or prism housings) 421 and 422, lenses (or lens housings) 431 and 440, a light source 430 and a stylus 435. The housing 410 contains an optical system with two or more imaging pathways as shown in FIG. 5 (e.g., imaging pathways 451 and 452 in FIG. 5). The optical axis 453 of the imaging apparatus 400 is separated by a specified angle(s) from the imaging pathways 451 and 452 produced by the imaging lenses 440 and 442 such that that an image can be formed on the image sensor 420 from different locations in the area defined by the field of view (e.g., the illumination region 448 in FIG. 5). The prisms 421 and 422 can focus or direct back the scattered light within the field of view of the image sensor 420 back to the image sensor 420. The shutters 446 and 446 and (optionally the prisms 421 and 422) can form at least a portion of the controller of the imaging apparatus 400, and can be controlled separately or in defined relationship to one another to select the optimal or desired imaging light path. FIG. 5 shows one image sensor 420 by way of example only, and not by limitation. In some configurations, two or more independent image sensors can be included in the imaging apparatus 400 either with or without dedicated shutters.

The imaging apparatus 400 can include a first optical component (e.g., the imaging lens 440) and a second optical component (e.g., the imaging lens 431) where each optical component (imaging lenses 431 and 440) is operatively coupled to the image sensor 420. The first optical component (e.g., the imaging lens 440) and the image sensor 420 can be collectively configured to define a first image pathway (e.g., image pathway 451 as seen by the dotted lines in FIG. 5) having an optical axis, and the second optical component (e.g., the imaging lens 431) and the image sensor 420 can be collectively configured to define a second image pathway (e.g., image pathway 452 in FIG. 5) having an optical axis. The non-imaging optical system has an optical axis non-parallel to the optical axis of the first image pathway 451 and the optical axis of the second image pathway 452.

The prism 421 and shutter 444 and any additional (optional) optical and/or electronic components (not shown in FIG. 5) along the first image pathway (e.g., image pathway 451 in FIG. 5) can form a first independent controller, and the prism 422 and shutter 446 and any additional (optional) optical and/or electronic components (not shown in FIG. 5) along the second image pathway (e.g., image pathway 452 in FIG. 5) can form a second independent controller. These independent controllers can be used to either select the first image pathway 451 or the second image pathway 452 that produces optimal or desired images on the image sensor 420 based on an orientation of the housing 410 relative to the surface of the film. This is because under certain orientations of the imaging apparatus 400, specular reflected light can reflect back into the image sensor 420 of the imaging apparatus 400 and can dominate the image if the specular reflected light is in the field of view of the image sensor 420. Such specular reflected light within the field of view can significantly reduce the contrast (and signal-noise-ratio) of the images formed on the image sensor 420. The specular reflected light can be prevented from striking (or being detected by) the image sensor 420 (or the amount of specular reflected light striking the image sensor 420 can be reduced or minimized) if the non-imaging optical system can output the illumination light on the surface such that the specular reflect light from either a first location or a second location within the illumination region 448 forms at a sufficiently large non-zero angle with respect to the optical axis of the image sensor 420 and the specular reflected light component has a lobe width less than the angle. In some orientations of the housing 410 with respect to the surface of the film, both the image pathways can be selected to produce the optimal image on the image sensor 420. In other orientations, because image pathways 451 and 452 observe the target area 448 from two different directions, at most, only one image pathway (451 or 452) will be flooded with specular reflection at a time as determined by the orientation of the housing 410 with respect to the surface of the film. Thus, the other image pathway (451 or 452) can be used to obtain a high quality image.

Similar to the embodiment shown in FIG. 3, the light source in the imaging apparatus 400 can be, for example, a semiconductor laser diode (instead of LEDs). In such instances, the laser light source can also generate a substantially collimated illumination beam. The substantially collimated illumination beam can propagate though one or more focusing lenses (not shown in FIG. 5) to produce an illumination region (e.g., illumination region 448 in FIGS. 4 and 5) on the surface of the target (e.g., a film or foil on a display surface). As described above, smaller illumination regions can improve the accuracy of detecting the location of the imaging apparatus 400 on the display surface. In such configurations, however, precise control of the distance between the focusing lens(es) and the surface of the film is desired. If the distance between the focusing lens(es) and the surface of the film is greater or less than the focal length of the focusing lens(es), then the size of the illumination region 448 will increase. In such instances, the effects of scattering and/or diffusion can lead to increase in size of the illumination region. Additionally, the amount of scattering and/or diffusion of the incident illumination beam along the x-axis can be either greater or less than that of the scattering and/or diffusion along the y-axis. In such instances, the shape of the illumination region 448 can also be affected.

Figure 6:
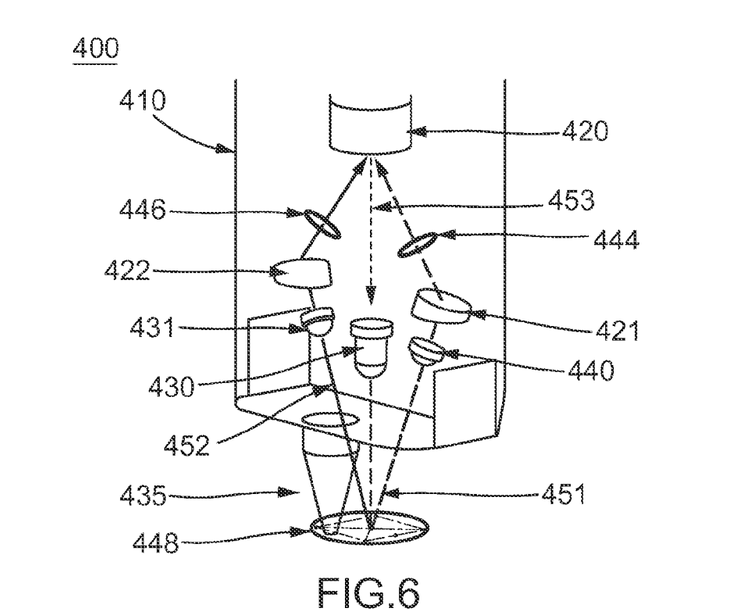
FIG. 6 is a three-dimensional (3-D) illustration of the cross-sectional image of the imaging apparatus in FIG. 5.

FIG. 6 is a three-dimensional (3-D) illustration of the cross-sectional image of the imaging apparatus in FIG. 5. FIG. 6 is a 3-D image of the imaging apparatus 400 that shows the two separate imaging pathways 451 and 452. In FIG. 6, the housing 410 of the imaging apparatus 400 is shown in a semi-transparent mode for viewing the different optical components contained within the housing 410. The imaging apparatus 400 includes the refractive optical components such as the prisms (or prism housings) 421 and 422, the lenses (or lens housings) 431 and 440, optical shutters 446 and 446, and the stylus 435 contained within the housing 410. The illumination light source 430 can be, for example, an LED and can be located in a portion of the housing 410 as shown in FIG. 6. Additionally, the image sensor 420 can be located, for example, within the housing 410 along the imaging pathways above the prisms 421 and 422. As described above, independent controllers (that can include the prisms, lenses and/or shutters) can be used to select the first imaging pathway (e.g., imaging pathway 451 as seen by the dashed lines in FIG. 6) or the second imaging pathway (e.g., imaging pathway 452 as seen by the solid lines in FIG. 6) that produces the optimal or desired images on (or detected by) the image sensor 420 based on the orientation of the housing 410 relative to the surface of the film.

Figure 7A:
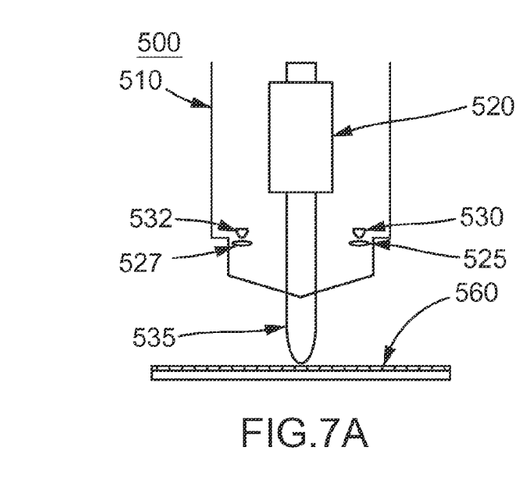
FIGS. 7A-C are diagrams of an imaging apparatus according to different embodiments.

Although FIGS. 1-6 described two separate embodiments of the imaging apparatus that were based on a dark-field direct illumination dual light optics assist configuration or a dark-field dual image path configuration, alternative embodiments of the imaging apparatus are possible. FIG. 7 summarizes some examples of possible embodiments. FIG. 7A shows a 2D cross-sectional image of an imaging apparatus 500 in the dark-field direct illumination dual light optics assist configuration. The imaging apparatus 500 includes a housing 510, an image sensor 520, light sources 530 and 532 (e.g., LED's), beam steering optical elements 525 and 527 (e.g., beam steering lenses or prisms), and a stylus 535. A film 560 contains the scattering microparticles. Operation of the imaging apparatus 500 shown in FIG. 7A is similar to the imaging apparatus 300 discussed in FIGS. 3 and 4.

Figure 7B:
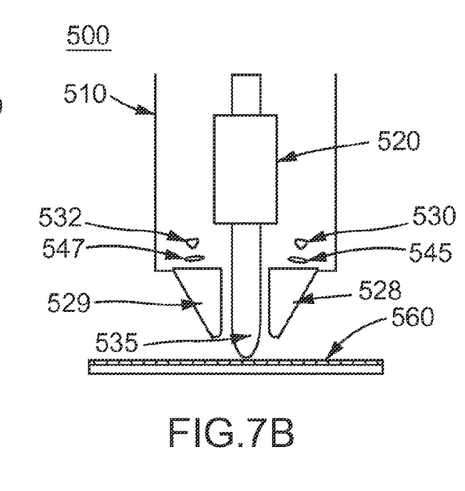

FIG. 7B shows a 2D cross-sectional image of an imaging apparatus 500 in another dark-field configuration. The imaging apparatus 500 shown in FIG. 7B includes a housing 510, an image sensor 520, light sources 530 and 532 (e.g., LED's), non-imaging beam shaping lenses 545 and 547, light guides 528 and 529, and a stylus 535. A film 560 contains the scattering microparticles. The non-imaging beam shaping lenses 545 and 547 can be used to control or alter the shape of the incident illumination beam. In some instances, when light-guides 528 and 529 are made of molded plastic, the functions of lenses of 547 and 545 can be incorporated into the plastic mold, and thus discrete components to implement such functions can be avoided.

Figure 7C:
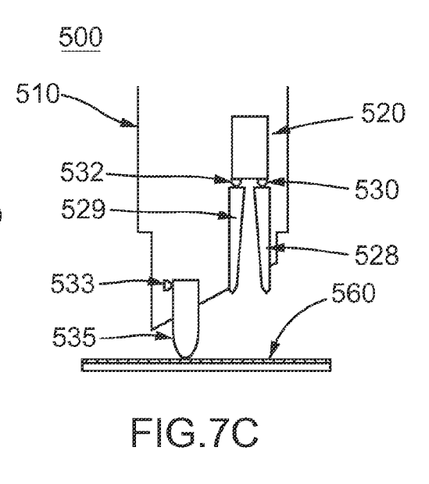

FIG. 7C shows a 2D cross-sectional image of an imaging apparatus 500, according to another embodiment. The imaging apparatus 500 shown in FIG. 11C includes a housing 510, an image sensor 520, light sources 530, 532 and 533 (e.g., LED's), a diffusion light guide 512, and a light guiding stylus 535. A film 560 contains the scattering microparticles. In such embodiments, the imaging system 500 can include an a primary illumination (light) source as defined by the LEDs 530 and 532 and the diffusion light guide 512, and an alternative illumination (light) source as defined by the LED 533 and the light guiding stylus 535.

The various embodiments of the imaging apparatus shown in FIGS. 3-7(A-C) can operate either in the dark-field imaging mode or the bright-field imaging mode. In such embodiments, a control module contained within the imaging apparatus that can implement signal processing functionalities can select a particular imaging modality (i.e., bright-field imaging or dark field-imaging) based on the instantaneous or near-instantaneous imaging conditions as described in greater detail herein. The control module that can adapt to either a bright-field or dark-field imaging situation that depends on the instantaneous geometrical orientation between the stylus and the surface of the film. Note that in such cases, it is not compulsory to have two or more or more non-imaging (illumination) sources, although more than one illumination source can be acceptable. Thus any of the embodiments disclosed in FIGS. 3-7(A-C) can operate in the light-filed or dark-field imaging mode if equipped with the appropriate signal processing functionality, and in such cases, the secondary non-imaging illumination source may optionally be omitted.

A control module (not shown in FIGS. 3-7(C)) that can implement signal processing functionalities and is associated with real time or near-real time image processing can select the imaging modality (i.e., either bright-field or dark-field) that is activated based on the instantaneous or near-instantaneous imaging conditions. The control module can be, for example, a hardware module and/or software module stored in a memory and/or executed in a processor on the printed circuit boards (PCB) of the imaging apparatus. For the dark-field image, providing satisfactory exclusion of specular reflection can be achieved and the appropriate image processing methods can be applied by the control module. As described in greater detail herein, the background of the final dark-field image formed at the image sensor will be dark and scattered light from the scattering microparticles will form white dots or spots. For the bright-field image, it is desirable to capture the specular reflected light. Hence, the background of the bright-field image formed on the image sensor will be bright while the location of the scattering microparticles will comparatively darker than the background due the substantially isotropic or substantially semi-isotropic scattering of the incident illumination by the scattering microparticles. Based on the quality of both the dark-field and bright-field image formed on the image sensor, the control module can select the proper method for detecting light spots on a dark background (dark-field imaging) or dark spots on a light background (bright-field imaging). Thus the imaging apparatus can implement a single imaging pathway for operation because at any given time, the imaging apparatus is operating in either the dark-field imaging mode or the bright-field imaging mode. In this embodiment, the optical, imaging and illumination systems remain constant and the image processing methods adapt to the current modality.

Figure 7D:
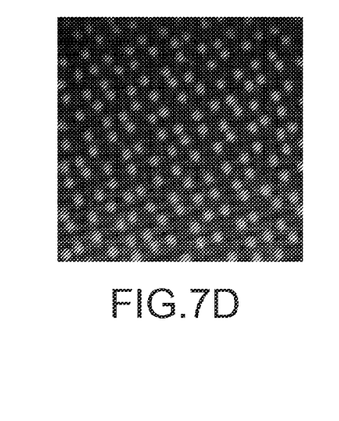
FIG. 7D is an example of a dark-field image of the scattering microparticles obtained by an imaging apparatus, according to an embodiment.

When producing the dark-field image, the specular reflected light is either prevented from striking (or being detected by) the image sensor (e.g., image sensor 520 in FIG. 7) or the amount of specular reflected striking (or being detected by) the image sensor is minimized. Hence, the background of the dark-field image that is formed on the image sensor is dark. The bright spots on the dark-field image appear from the scattered reflection from the scattering microparticles. FIG. 7D shows an example of such a dark-field image. When producing the bright-field image, the specular reflected light is allowed to strike (or be detected by) the image sensor. Hence, the background of the bright-field image that is formed on the image sensor is bright. The dark spots on the bright-field image appear from the scattering microparticles because the scattered reflection (which can be isotropic) from the microparticles reduces the intensity of light reaching the field of view of the image sensor. Hence, light scattered by microparticles appear within an image as comparatively dark with respect to the background.

Figure 8:
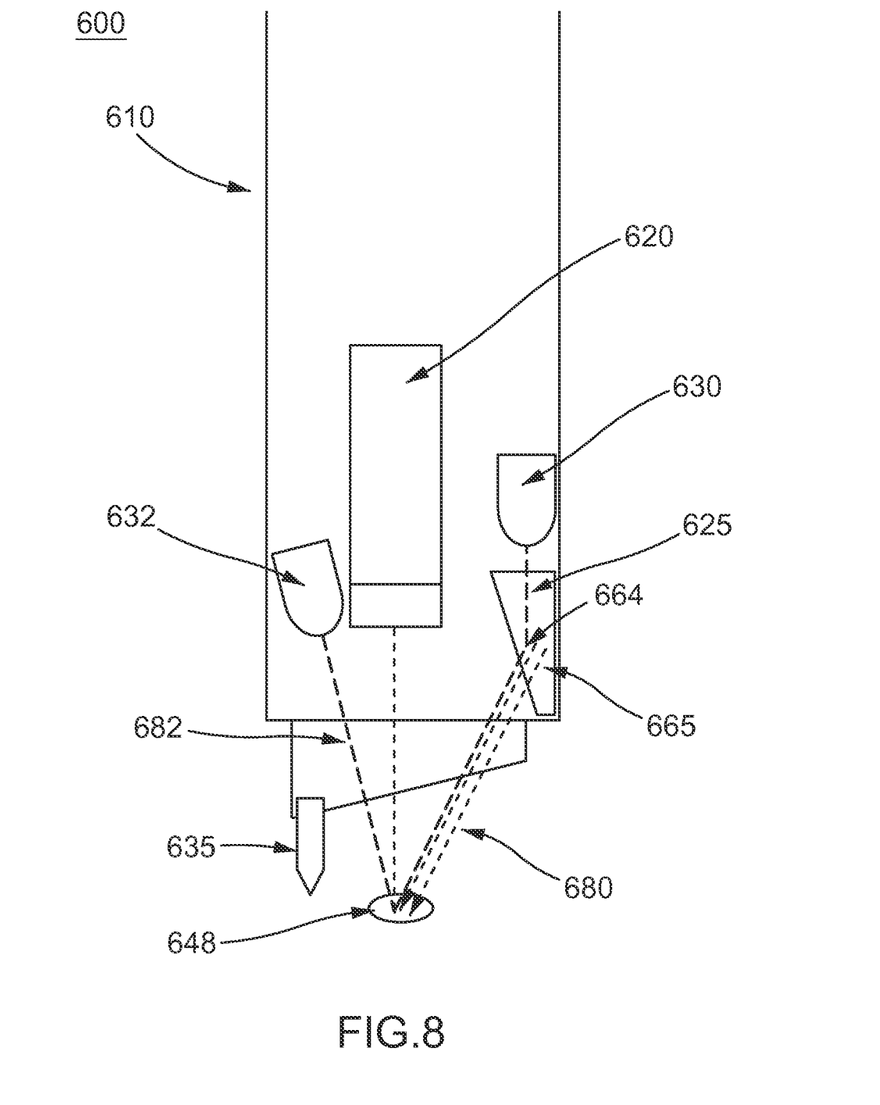
FIG. 8 is a two-dimensional (2-D) cross-section diagram of an imaging apparatus, according to yet another embodiment.

FIG. 8 is a two-dimensional (2-D) cross-section diagram of an imaging apparatus, according to yet another embodiment. In such embodiments, the imaging apparatus illustrates the use of beam steering components and an asymmetric distribution of the non-imaging (illumination) light sources. The imaging apparatus 600 can include an image sensor 620 coupled to or disposed within a housing 610 and having a field of view. The imaging apparatus 600 can include a first non-imaging optical system coupled to the housing 610 that includes a first light source (e.g., LED 630) and a first set of beam steering optical elements (e.g., prism 625) coupled to the housing 610. In such embodiments, the first non-imaging optical system can output (either diffuse or non-diffuse) light in multiple directions from at least a first location 664 and a second location 665 (or multiple locations) of the first non-imaging optical system to produce the (either diffuse or non-diffuse) light illumination pathway 680. The image sensor 620 can receive from a surface of the film at least one of (1) a scattered light component associated with the first location, or (2) a scattered light component associated with the second location. In such embodiments, the image sensor 620 and the first non-imaging optical system can be configured such that the image sensor 620, during operation, does not receive a specular reflected light component associated with the first location and a specular reflected light component associated with the second location to form an optimal dark-field image on the image sensor 620.

The imaging apparatus 600 can also include a second non-imaging optical system coupled to the housing 610 that includes a second light source (e.g., LED 632) and, optionally, a second set of optical elements (not shown in FIG. 12) coupled to or disposed within the housing 610. The second non-imaging optical system can output light to the surface of the film to produce the light illumination pathway 682 that produces a specular reflected light component and/or a scattered light component from the scattering microparticles on the surface of the film. In some instances, the image sensor 620 and the second non-imaging optical system can be collectively configured such that, during operation, the image sensor 620 receives at least a portion of the specular reflected light component output by the surface of the film after being impinged upon by the illumination light from the light illumination pathway 682. In other instances, the image sensor 620 and the second non-imaging optical system can be collectively configured such that, during operation, the image sensor 620 receives at least a portion of the scattered light component from the scattering microparticles on the surface of the film and does not receive a specular reflected light component.

Note that the angle of incidence of the first light illumination pathway 680 is not equal to the angle of incidence of the second first light illumination pathway 682. One or more beam steering optical elements (e.g., prism 625) can be used to vary the angle of incidence of the light illumination pathway (either illumination pathway 680 or illumination pathway 682) to account for topographical variations as the stylus 635 moves over the surface of the film due to, for example, manufacturing imperfections, changes in the user's positioning of the stylus 735, etc. These topographical variations can lead to changes in the angle of the scattered light (from the scattering microparticles) with respect to the image sensor 620. Additionally, the asymmetric distribution of the (non-imaging) light illumination pathways can allow one of the light illumination pathways (either illumination pathway 680 or illumination pathway 682) to be more suitable to illuminate the surface of the film according to different orientations of the stylus 635 with respect to the film. As described above, the embodiment of the imaging apparatus 600 can also be operated in either the dark-field imaging mode or the bright-field imaging mode if a control module can be included in the imaging apparatus 600 that can implement specific signal processing functionalities.

The embodiments of the imaging apparatus discussed in FIGS. 1-8 deal with receiving (or rejecting) the specular reflected light and the scattered light from the scattering microparticles contained within the display film. In other embodiments, however, the imaging apparatus can involve receiving a fluorescent signal generated by fluorescent microparticles embedded within the surface of the display film (instead of scattering microparticles). In such embodiments, the microparticles used can be transparent and can be impregnated with a fluorescent compound that can be tuned to fluoresce at certain wavelengths. One example can involve using fluorescent microparticle that can be excited by the imaging apparatus at ultra-violet (UV) wavelengths and generating fluorescence at infra-red (IR) wavelengths. The large Stokes shift (difference between the excitation wavelength and the emission wavelength of the fluorescent microparticles) can be used to improve the signal-noise ratio of the image formed at the image sensor of the imaging apparatus. In such embodiments, the imaging apparatus can be configured to respond to the IR fluorescence signal and reject all specular reflected light in the UV range. The rejection of the specular reflected light and/or any bleedthrough of the excitation illumination in the UV range can be implemented by using the appropriate emission filters in the imaging pathways. This configuration, however, can involve the addition of more optical components in the imaging apparatus (e.g., excitation filters, emission filters, etc.).

Any of the imaging apparatus described herein can include any suitable processor such that the generator and/or module performs the functions described herein. Such processors can be a general-purpose processor (e.g., a central processing unit (CPU)) or other processor configured to execute one or more instructions stored in the memory. In some embodiments, the processor can alternatively be an application-specific integrated circuit (ASIC) or a field programmable gate array (FPGA). The processor can be configured to execute specific modules and/or sub-modules that can be, for example, hardware modules, software modules stored in the memory and executed in the processor, and/or any combination thereof. The memory included in the imaging apparatus can be, for example, flash memory, one time programmable memory, a random access memory (RAM), a memory buffer, a hard drive, a read-only memory (ROM), an erasable programmable read-only memory (EPROM), and/or so forth. In some embodiments, the memory includes a set of instructions to cause the processor to execute modules, processes and/or functions used to generate, control, amplify, and/or transfer electric current to another portion of the imaging apparatus.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

Although various embodiments have been described as having particular features and/or combinations of components, other embodiments are possible having a combination of any features and/or components from any of embodiments where appropriate. For example, any of the embodiments of the imaging apparatus described herein can include multiple light sources, multiple imaging sensors with integrated control electronics for decoding the co-ordinates of the position-coding patterns on the display surface, and transmitters for transmitting the position co-ordinates to an external device.

What is claimed is:

1. An apparatus, comprising:
a housing;
an image sensor coupled to the housing;
a first non-imaging optical system coupled to the housing and configured to output light to a surface to produce a scattered light component and a first specular reflected light component,
the image sensor and the first non-imaging optical system collectively configured such that, during operation, the image sensor receives from a surface (1) at least a portion of the scattered light component and not the first specular reflected light component or (2) at least a portion of the scattered light component having a magnitude and at least a portion of the first specular reflective light component having a magnitude less than the magnitude of the portion of the scattered light component; and
a second non-imaging optical system coupled to the housing and configured to output light to the surface to produce a second secular reflected light component; and
a controller configured to selectively deactivate the first non-imaging optical system and the second non-imaging optical system based on at least one of the magnitude of the first specular reflective light component received by the image sensor or a magnitude of the second specular reflective light component received by the image sensor.

2. The apparatus of claim 1, wherein:
the image sensor has a field of view and an optical axis;
the first non-imaging optical system configured to output light to produce the first specular reflected light component at a non-zero angle relative to the optical axis of the image sensor, the first specular reflected light component having a lobe width less than the angle.

3. The apparatus of claim 1, wherein:
the image sensor has a field of view,
the first non-imaging optical system is configured to send light along a first optical path from at least a first location of the housing, and
the second non-imaging optical system is configured to send light along a second optical path from at least a second location of the housing, at least a portion of the field of view being between the first location and the second location.

4. The apparatus of claim 1, wherein:
the image sensor has a field of view,
the first non-imaging optical system includes a first light source, a first refractive optical component, and a first reflective optical component collectively configured to send light along a first optical path from at least a first location of the housing, and the second non-imaging optical system includes a second light source, a second refractive optical component and a second reflective optical component collectively configured to send light along a second optical path from at least a second location of the housing, at least a portion of the field of view being between the first location and the second location.

5. The apparatus of claim 1, wherein:
the first non-imaging optical system and the image sensor are collectively configured to define a first image path having an optical axis, and
the second non-imaging optical system and the image sensor are collectively configured to define a second image path having an optical axis, the apparatus further comprising:
a light source having an optical axis non-parallel to the optical axis of the first image path and the optical axis of the second image path.

6. The apparatus of claim 1, wherein:
the image sensor and the first non-imaging optical system are collectively configured such that, during operation, the image sensor receives at least a portion of the first specular reflected light component, a magnitude of the first specular reflected light component being greater than the magnitude of the scattered light component.

7. An apparatus, comprising:
a housing;
an image sensor coupled to the housing and having a field of view;
a non-imaging optical system coupled to the housing, the non-imaging optical system including a first light source configured to output light from at least a first location of the housing and a second light source configured to output light from at least a second location of the housing, at least a portion of the field of view being between and excluding the first location and the second location,
the image sensor configured to receive from a surface at least one of (1) a scattered light component associated with the first location, or (2) a scattered light component associated with the second location,
the image sensor configured to receive from the surface a specular light component associated with the first light source and having a first magnitude when the housing is in a first orientation relative to the surface,
the image sensor configured to receive from the surface a specular light component associated with the first light source and having a second magnitude when the housing is in a second orientation relative to the surface; and
a controller configured to selectively deactivate the first light source based on at least one of the first magnitude or the second magnitude.

8. The apparatus of claim 7, wherein:
the image sensor has an optical axis, and
the non-imaging optical system is configured to output light to produce a specular reflected light component from the first location at a non-zero angle relative to the optical axis of the image sensor, the specular reflected light component having a lobe width less than the angle.

9. The apparatus of claim 7, wherein:
the non-imaging optical system includes, a first optical component, and a second optical component,
the first light source and the first optical component are collectively configured to send light along a first optical path from at least the first location to the surface, and
the second light source and the second optical component are collectively configured to send light along a second optical path from at least the second location to the surface, at least a portion of the field of view being between the first location and the second location.

10. The apparatus of claim 7, wherein:
the image sensor and the non-imaging optical system are collectively configured such that the image sensor, does not receive a specular light component associated with the first location when the first light source is active and the housing is in the first orientation relative to the surface,
the image sensor and the non-imaging optical system are collectively configured such that the image sensor would receive a secular light component associated with the second location when the second light source is active and the housing is in the first orientation relative to the surface, and
the controller is configured to deactivate the second light source when the housing is in the second location such that the image sensor does not receive the specular light component associated with the second location and the second light source when the housing is in the first orientation relative to the surface.

11. The apparatus of claim 7, wherein:
the image sensor and the non-imaging optical system are collectively configured such that the image sensor (1) does not receive a specular reflected light component associated with the first location when the housing is in the first orientation relative to the housing or (2) receives a specular reflected light component associated with the first location when the housing is in the first orientation relative to the housing and having a magnitude less than a magnitude of the at least one of the scattered light component associated with the first location or the scattered light component associated with the second location.

12. An apparatus, comprising:
a stylus housing configured to be used with an electronic device;
an image sensor coupled to the stylus housing, the image sensor defining an optical axis and a field of view; and
a non-imaging optical system coupled to the stylus housing and configured to output light to a surface along a first optical path when the stylus housing is in a first orientation relative to the surface, the first optical path having an optical axis non-parallel to the optical axis of the image sensor to produce a first specular reflection,
the non-imaging optical system configured to output light to the surface along a second optical path when the stylus housing is in a second orientation relative to the surface to produce a second specular reflection,
a controller configured to prevent light from being output from at least one of the first optical path or the second optical path such that the image sensor does not receive the first specular reflection and the second specular reflection.

13. The apparatus of claim 12, wherein:
the non-imaging optical system is configured to output light to the surface to produce a scattered light component, and
the image sensor and the non-imaging optical system are collectively configured such that, during operation, the image sensor receives at least a portion of the scattered light component.

14. The apparatus of claim 12, wherein:
the non-imaging optical system is configured to output light from the first optical path at least a first location of the stylus housing, and the non-imaging optical system is configured to output light from the second optical path at least a second location of the stylus housing, at least a portion of the field of view being between the first location and the second location.

15. The apparatus of claim 12, further comprising:
a first optical component and a second optical component each operatively coupled to the image sensor, the first optical component and the image sensor collectively configured to define a first image path having an optical axis, the second optical component and the image sensor collectively configured to define a second image path having an optical axis,
the non-imaging optical system including a light source having an optical axis non-parallel to the optical axis of the first image path and the optical axis of the second image path.

16. The apparatus of claim 12, wherein the first orientation is associated with an axis of stylus housing being disposed at a first oblique angle relative to the surface and the second orientation is associated with the axis of the stylus housing being disposed at a second oblique angle relative to the surface, the first oblique angle different from the second oblique angle.

17. The apparatus of claim 7, wherein the first orientation is associated with an axis of stylus housing being disposed at a first oblique angle relative to the surface and the second orientation is associated with the axis of the stylus housing being disposed at a second oblique angle relative to the surface, the first oblique angle different from the second oblique angle.

\* \* \* \* \*